United States Patent
Doan et al.

(10) Patent No.: US 11,399,575 B2
(45) Date of Patent: Aug. 2, 2022

(54) WEARABLE DEVICE AND APPLICATION FOR BEHAVIORAL SUPPORT

(71) Applicant: GlaxoSmithKline Consumer Healthcare Holdings, US, LLC, Wilmington, DE (US)

(72) Inventors: Brian Doan, Warren, NJ (US); Jeffrey Brunner, Warren, NJ (US); Alexander James Peacop, Worcestershire (GB); Martin Crofton, West Midlands (GB)

(73) Assignee: GLAXOSMITHKLINE CONSUMER HEALTHCARE HOLDINGS (US) LLC, Wilmington, DE (US)

( * ) Notice: Subject to any disclaimer, the term of this patent is extended or adjusted under 35 U.S.C. 154(b) by 1092 days.

(21) Appl. No.: 16/002,263

(22) Filed: Jun. 7, 2018

(65) Prior Publication Data

US 2019/0037919 A1    Feb. 7, 2019

Related U.S. Application Data

(60) Provisional application No. 62/665,081, filed on May 1, 2018, provisional application No. 62/540,116, filed on Aug. 2, 2017.

(51) Int. Cl.
*A24F 47/00* (2020.01)
*G06F 1/16* (2006.01)
(Continued)

(52) U.S. Cl.
CPC ............ *A24F 47/00* (2013.01); *A44C 5/0023* (2013.01); *G06F 1/163* (2013.01); *G09B 5/02* (2013.01);
(Continued)

(58) Field of Classification Search
CPC ....... A24F 47/00; A44C 5/0023; G06F 1/163; G09B 5/02
See application file for complete search history.

(56) References Cited

U.S. PATENT DOCUMENTS

| 4,853,854 A | 8/1989 | Behar et al. |
| 5,285,430 A | 2/1994 | Decker |

(Continued)

FOREIGN PATENT DOCUMENTS

| EP | 1224522 A2 | 7/2002 |
| EP | 2115722 A2 | 11/2009 |

(Continued)

*Primary Examiner* — David E Choi
(74) *Attorney, Agent, or Firm* — Roshni A. Sitapara

(57) ABSTRACT

Embodiments can provide a wearable device for nicotine cessation behavioral support, comprising a top surface; a first surface; a second surface; an underside surface; a communication device; one or more buttons; an internal storage medium; and a power supply; wherein the one or more buttons are configured to log a NRT use event to the internal storage medium when depressed and subsequently released within a predetermined timeframe; wherein the one or more buttons are configured to log a tobacco use event to the internal storage medium when depressed and released at a time longer than the predetermined timeframe; wherein the one or more buttons, when depressed, are configured to log a craving event to the internal storage medium, wherein an intensity of the craving event is determined by a time duration between depression and release of the one or more buttons.

25 Claims, 12 Drawing Sheets

(51) Int. Cl.
  *G09B 5/02* (2006.01)
  *G09B 19/00* (2006.01)
  *A44C 5/00* (2006.01)
  *A61B 5/024* (2006.01)
(52) U.S. Cl.
  CPC .............. *G09B 19/00* (2013.01); *A61B 5/024* (2013.01); *A61B 5/02438* (2013.01)

(56) References Cited

U.S. PATENT DOCUMENTS

| | | | |
|---|---|---|---|
| 5,813,026 | A | 9/1998 | Borg et al. |
| 5,822,715 | A | 10/1998 | Worthington et al. |
| 5,833,466 | A | 11/1998 | Borg |
| 5,908,301 | A | 6/1999 | Lutz |
| 5,956,501 | A | 9/1999 | Brown |
| 5,967,789 | A | 10/1999 | Segel et al. |
| 6,167,362 | A | 12/2000 | Brown |
| D440,352 | S | 4/2001 | Gore et al. |
| 6,233,539 | B1 | 5/2001 | Brown |
| 6,305,839 | B1 | 10/2001 | Krstulovic |
| 6,379,301 | B1 | 4/2002 | Worthington et al. |
| 6,605,038 | B1 | 8/2003 | Teller et al. |
| 6,606,997 | B2 | 8/2003 | Brue |
| 6,769,915 | B2 | 8/2004 | Murgia et al. |
| D509,760 | S | 9/2005 | Burrell et al. |
| 7,015,796 | B2 | 3/2006 | Snyder |
| 7,028,693 | B2 | 4/2006 | Brue |
| 7,167,818 | B2 | 1/2007 | Brown |
| D549,602 | S | 8/2007 | Oberrieder et al. |
| D550,105 | S | 9/2007 | Oberrieder et al. |
| D560,520 | S | 1/2008 | Oberrieder et al. |
| 7,392,167 | B2 | 6/2008 | Brown |
| D596,510 | S | 7/2009 | Register et al. |
| 7,610,919 | B2 | 11/2009 | Utley et al. |
| 7,643,971 | B2 | 1/2010 | Brown |
| D610,922 | S | 3/2010 | Lammers-Meis et al. |
| 7,689,437 | B1 | 3/2010 | Teller et al. |
| 7,725,842 | B2 | 5/2010 | Bronkema |
| 7,912,684 | B2 | 3/2011 | Brown |
| 7,912,688 | B2 | 3/2011 | Brown |
| 7,920,998 | B2 | 4/2011 | Brown |
| 7,937,254 | B2 | 5/2011 | Brown |
| 7,937,255 | B2 | 5/2011 | Brown |
| 7,941,308 | B2 | 5/2011 | Brown |
| 7,949,507 | B2 | 5/2011 | Brown |
| 7,959,567 | B2 | 6/2011 | Stivoric et al. |
| 7,979,259 | B2 | 7/2011 | Brown |
| 8,073,707 | B2 | 12/2011 | Teller et al. |
| RE43,316 | E | 4/2012 | Brown et al. |
| D657,697 | S | 4/2012 | Lammers-Meis et al. |
| D660,726 | S | 5/2012 | Register et al. |
| D661,206 | S | 6/2012 | Register et al. |
| 8,303,500 | B2 | 11/2012 | Raheman |
| 8,314,591 | B2 | 11/2012 | Terry et al. |
| 8,402,976 | B2 | 3/2013 | Fernando et al. |
| D682,712 | S | 5/2013 | Lammers-Meis et al. |
| 8,533,007 | B2 | 9/2013 | Egami et al. |
| 8,635,054 | B2 | 1/2014 | Brown |
| 8,659,418 | B2 | 2/2014 | Kreml |
| D715,668 | S | 10/2014 | Roush et al. |
| 8,851,081 | B2 | 10/2014 | Fernando et al. |
| D718,647 | S | 12/2014 | Roush et al. |
| 8,926,320 | B2 | 1/2015 | Al Gharib |
| 8,961,413 | B2 | 2/2015 | Teller et al. |
| D724,468 | S | 3/2015 | Tan et al. |
| D725,497 | S | 3/2015 | Henne et al. |
| 9,033,875 | B2 | 5/2015 | Teller et al. |
| 9,037,578 | B2 | 5/2015 | Brust et al. |
| D733,604 | S | 7/2015 | Tan et al. |
| 9,095,175 | B2 | 8/2015 | Terry et al. |
| 9,110,958 | B2 | 8/2015 | Brust et al. |
| D737,716 | S | 9/2015 | Tan et al. |
| D738,769 | S | 9/2015 | Tan et al. |
| D739,268 | S | 9/2015 | Lammers-Meis et al. |
| D739,768 | S | 9/2015 | Hanshew et al. |
| D740,136 | S | 10/2015 | Henne et al. |
| 9,171,048 | B2 | 10/2015 | Brust et al. |
| D742,254 | S | 11/2015 | Greusel et al. |
| D742,761 | S | 11/2015 | Grazian et al. |
| 9,183,262 | B2 | 11/2015 | Brust et al. |
| 9,295,285 | B2 | 3/2016 | Glazer |
| D756,240 | S | 5/2016 | Register et al. |
| D757,583 | S | 5/2016 | Roush et al. |
| 9,420,971 | B2 | 8/2016 | David et al. |
| 9,429,432 | B2 | 8/2016 | McClernon et al. |
| 9,430,617 | B2 | 8/2016 | Brust et al. |
| 9,439,455 | B2 | 9/2016 | Alarcon et al. |
| 9,459,938 | B1 | 10/2016 | Denton et al. |
| 9,462,832 | B2 | 10/2016 | Lord |
| D772,081 | S | 11/2016 | Lee et al. |
| 9,504,278 | B2 | 11/2016 | Liu |
| 9,540,691 | B2 * | 1/2017 | Fava .................. C12Q 1/6883 |
| 2001/0027794 | A1 | 10/2001 | Brue |
| 2001/0047252 | A1 | 11/2001 | Brown |
| 2002/0086271 | A1 | 7/2002 | Murgia et al. |
| 2002/0114223 | A1 | 8/2002 | Perlman et al. |
| 2003/0108850 | A1 | 6/2003 | Murgia et al. |
| 2004/0016437 | A1 | 1/2004 | Cobb et al. |
| 2004/0031498 | A1 | 2/2004 | Brue |
| 2004/0034289 | A1 | 2/2004 | Teller et al. |
| 2004/0201480 | A1 | 10/2004 | Snyder |
| 2004/0247748 | A1 | 12/2004 | Bronkema |
| 2005/0021372 | A1 | 1/2005 | Mikkelsen et al. |
| 2005/0043965 | A1 | 2/2005 | Heller et al. |
| 2005/0141346 | A1 | 6/2005 | Rawls et al. |
| 2005/0263160 | A1 | 12/2005 | Utley et al. |
| 2006/0031102 | A1 | 2/2006 | Teller et al. |
| 2006/0099554 | A1 | 5/2006 | Frost |
| 2006/0200322 | A1 | 9/2006 | Blondal et al. |
| 2006/0224051 | A1 | 10/2006 | Teller et al. |
| 2007/0032997 | A1 | 2/2007 | Brown |
| 2007/0055486 | A1 | 3/2007 | Brown |
| 2007/0078681 | A1 | 4/2007 | Brown |
| 2007/0118348 | A1 | 5/2007 | Brown |
| 2007/0168501 | A1 | 7/2007 | Cobb et al. |
| 2007/0282930 | A1 | 12/2007 | Leftwich et al. |
| 2008/0029109 | A1 | 2/2008 | Hercules |
| 2008/0052057 | A1 | 2/2008 | Brown |
| 2008/0097180 | A1 | 4/2008 | Brown |
| 2008/0103380 | A1 | 5/2008 | Brown |
| 2008/0108888 | A1 | 5/2008 | Brown |
| 2008/0109197 | A1 | 5/2008 | Brown |
| 2008/0171918 | A1 | 7/2008 | Teller et al. |
| 2008/0177158 | A1 | 7/2008 | Teller et al. |
| 2008/0183051 | A1 | 7/2008 | Teller et al. |
| 2008/0183052 | A1 | 7/2008 | Teller et al. |
| 2008/0275309 | A1 | 11/2008 | Kasabach et al. |
| 2008/0294028 | A1 | 11/2008 | Brown |
| 2008/0319797 | A1 | 12/2008 | Egami et al. |
| 2009/0118590 | A1 | 5/2009 | Stivoric et al. |
| 2009/0248380 | A1 | 10/2009 | Brown |
| 2009/0320863 | A1 | 12/2009 | Fernando et al. |
| 2010/0003653 | A1 | 1/2010 | Brown |
| 2010/0015584 | A1 | 1/2010 | Singer et al. |
| 2010/0100391 | A1 | 4/2010 | Daya et al. |
| 2010/0144795 | A1 * | 6/2010 | Bain ..................... A61P 25/28 514/338 |
| 2010/0209897 | A1 | 8/2010 | Keith et al. |
| 2010/0218118 | A1 | 8/2010 | Bronkema |
| 2010/0305967 | A1 | 12/2010 | Daya et al. |
| 2010/0305975 | A1 | 12/2010 | Daya et al. |
| 2011/0046519 | A1 | 2/2011 | Raheman |
| 2011/0123969 | A1 | 5/2011 | Boettcher et al. |
| 2011/0151418 | A1 | 6/2011 | Delespaul et al. |
| 2011/0152635 | A1 | 6/2011 | Morris et al. |
| 2011/0183305 | A1 | 7/2011 | Orbach |
| 2011/0199205 | A1 | 8/2011 | Kreml |
| 2011/0247638 | A1 | 10/2011 | Ayala |
| 2011/0265806 | A1 | 11/2011 | Alarcon et al. |
| 2011/0270053 | A1 | 11/2011 | Utley et al. |
| 2011/0277764 | A1 | 11/2011 | Minskoff et al. |
| 2011/0277780 | A1 | 11/2011 | Minskoff et al. |
| 2011/0278189 | A1 | 11/2011 | Minskoff et al. |

(56) References Cited

U.S. PATENT DOCUMENTS

| | | |
|---|---|---|
| 2012/0010592 A1 | 1/2012 | Brown |
| 2012/0059230 A1 | 3/2012 | Teller et al. |
| 2012/0101630 A1 | 4/2012 | Daya et al. |
| 2012/0214107 A1 | 8/2012 | Al Gharib |
| 2012/0252580 A1 | 10/2012 | Dugan |
| 2012/0253487 A1 | 10/2012 | Dugan |
| 2012/0253489 A1 | 10/2012 | Dugan |
| 2013/0123719 A1 | 5/2013 | Mao et al. |
| 2013/0130789 A1 | 5/2013 | Brigham et al. |
| 2013/0206154 A1 | 8/2013 | Fernando et al. |
| 2013/0216989 A1 | 8/2013 | Cuthbert |
| 2013/0284192 A1 | 10/2013 | Peleg et al. |
| 2013/0319439 A1 | 12/2013 | Gorelick et al. |
| 2013/0340775 A1 | 12/2013 | Juster et al. |
| 2014/0012593 A1 | 1/2014 | Kim |
| 2014/0081666 A1 | 3/2014 | Teller et al. |
| 2014/0088995 A1 | 3/2014 | Damani |
| 2014/0088996 A1 | 3/2014 | Damani |
| 2014/0089836 A1 | 3/2014 | Damani et al. |
| 2014/0096781 A1 | 4/2014 | Sears et al. |
| 2014/0096782 A1 | 4/2014 | Ampolini et al. |
| 2014/0116455 A1 | 5/2014 | Youn |
| 2014/0142965 A1 | 5/2014 | Houston et al. |
| 2014/0156308 A1 | 6/2014 | Ohnemus et al. |
| 2014/0156645 A1 | 6/2014 | Brust |
| 2014/0156646 A1 | 6/2014 | Brust |
| 2014/0156676 A1 | 6/2014 | Brust |
| 2014/0157171 A1 | 6/2014 | Brust |
| 2014/0202477 A1 | 7/2014 | Qi |
| 2014/0221787 A1 | 8/2014 | Teller et al. |
| 2014/0221788 A1 | 8/2014 | Teller et al. |
| 2014/0235293 A1 | 8/2014 | Sheldon |
| 2014/0236025 A1 | 8/2014 | Sheldon |
| 2014/0246034 A1 | 9/2014 | Terry et al. |
| 2014/0246035 A1 | 9/2014 | Minskoff et al. |
| 2014/0272844 A1 | 9/2014 | Hendriks et al. |
| 2014/0272845 A1 | 9/2014 | Hendriks et al. |
| 2014/0305450 A1 | 10/2014 | Xiang |
| 2014/0316220 A1 | 10/2014 | Sheldon |
| 2014/0321245 A1 | 10/2014 | Sharpe |
| 2014/0358018 A1 | 12/2014 | Neagle, III |
| 2014/0365111 A1 | 12/2014 | McClernon et al. |
| 2015/0007838 A1 | 1/2015 | Fernando et al. |
| 2015/0024355 A1 | 1/2015 | Ghofrani et al. |
| 2015/0053214 A1 | 2/2015 | Alarcon et al. |
| 2015/0059779 A1 | 3/2015 | Alarcon et al. |
| 2015/0064672 A1 | 3/2015 | Bars |
| 2015/0065825 A1 | 3/2015 | Utley et al. |
| 2015/0066174 A1 | 3/2015 | Dugan |
| 2015/0118662 A1 | 4/2015 | Ellison et al. |
| 2015/0142387 A1 | 5/2015 | Alarcon et al. |
| 2015/0164144 A1 | 6/2015 | Liu |
| 2015/0186614 A1 | 7/2015 | Daya et al. |
| 2015/0196053 A1 | 7/2015 | Liu |
| 2015/0199490 A1 | 7/2015 | Iancu et al. |
| 2015/0199493 A1 | 7/2015 | Glenn et al. |
| 2015/0208723 A1 | 7/2015 | Glazer |
| 2015/0220706 A1 | 8/2015 | Lin et al. |
| 2015/0224268 A1 | 8/2015 | Henry et al. |
| 2015/0245660 A1 | 9/2015 | Lord |
| 2015/0257448 A1 | 9/2015 | Lord |
| 2015/0262497 A1 | 9/2015 | Landau et al. |
| 2015/0272212 A1 | 10/2015 | Pedrell |
| 2015/0304401 A1 | 10/2015 | Liu |
| 2015/0304402 A1 | 10/2015 | Liu |
| 2015/0310760 A1 | 10/2015 | Knotts et al. |
| 2015/0327596 A1 | 11/2015 | Alarcon et al. |
| 2015/0347689 A1 | 12/2015 | Neagle |
| 2015/0356261 A1 | 12/2015 | Brust et al. |
| 2015/0364057 A1 | 12/2015 | Catani et al. |
| 2015/0366268 A1 | 12/2015 | Shabat |
| 2015/0374301 A1 | 12/2015 | Teller et al. |
| 2016/0007651 A1 | 1/2016 | Ampolini et al. |
| 2016/0029693 A1 | 2/2016 | Klein et al. |
| 2016/0029698 A1 | 2/2016 | Xiang |
| 2016/0081393 A1 | 3/2016 | Black |
| 2016/0103921 A1 | 4/2016 | Brust et al. |
| 2016/0132604 A1 | 5/2016 | Brust et al. |
| 2016/0171180 A1 | 6/2016 | Yagnyamurthy et al. |
| 2016/0189216 A1 | 6/2016 | Liu |
| 2016/0192880 A9 | 7/2016 | Utley et al. |
| 2016/0217266 A1 | 7/2016 | Damani et al. |
| 2016/0219931 A1 | 8/2016 | Doshi et al. |
| 2016/0219938 A1 | 8/2016 | Mamoun et al. |
| 2016/0220798 A1 | 8/2016 | Netzel et al. |
| 2016/0227842 A1 | 8/2016 | Xiang |
| 2016/0255878 A1 | 9/2016 | Huang et al. |
| 2016/0260156 A1 | 9/2016 | Liu |
| 2016/0263482 A1 | 9/2016 | Xiang |
| 2016/0275254 A1 | 9/2016 | Mahoney |
| 2016/0275262 A1 | 9/2016 | Panayotov et al. |
| 2016/0278435 A1 | 9/2016 | Choukroun et al. |
| 2016/0285983 A1 | 9/2016 | Liu |
| 2016/0287142 A1 | 10/2016 | Han et al. |
| 2016/0321879 A1 | 11/2016 | Oh et al. |
| 2016/0323404 A1 | 11/2016 | Liu |
| 2016/0324469 A1 | 11/2016 | Utley et al. |
| 2016/0331025 A1 | 11/2016 | Cameron |
| 2016/0331027 A1 | 11/2016 | Cameron |
| 2016/0331035 A1 | 11/2016 | Cameron |
| 2016/0331037 A1 | 11/2016 | Cameron |
| 2016/0337141 A1 | 11/2016 | Cameron |
| 2016/0337362 A1 | 11/2016 | Cameron |
| 2016/0337444 A1 | 11/2016 | Cameron |
| 2016/0342767 A1 | 11/2016 | Narasimhan et al. |
| 2016/0351070 A1 | 12/2016 | Aillon-Sohl |
| 2017/0055573 A1* | 3/2017 | Utley .................. G08B 21/12 |
| 2019/0015612 A1* | 1/2019 | Marmur ................ A24F 40/42 |
| 2019/0037919 A1* | 2/2019 | Doan ..................... G09B 5/02 |
| 2021/0145844 A1* | 5/2021 | Blackburn ........... A61K 31/352 |
| 2021/0202066 A1* | 7/2021 | Chancellor ........... G16H 80/00 |

FOREIGN PATENT DOCUMENTS

| | | |
|---|---|---|
| EP | 2967355 A2 | 1/2016 |
| EP | 3010570 A2 | 4/2016 |
| WO | WO 2016/145373 A1 | 9/2016 |

\* cited by examiner

WEARABLE DEVICE AND APPLICATION FOR BEHAVIORAL SUPPORT

TECHNOLOGY FIELD

The present device relates to a wearable device that can be used in conjunction with an application on a mobile device to aid a user in quitting tobacco. In addition to providing the quitter motivation and education, the mobile application can be used in conjunction with nicotine replacement therapies (NRT).

BACKGROUND

Trying to quit the use of tobacco products (such as cigarettes, cigars, or chewing tobacco) is an intense personal battle, one which can take years to complete and can involve many stops and re-starts. Progress is slow due to the addictive nature of nicotine and the habitual need to smoke as part of peoples' daily routines. NRT products have shown success by substituting the nicotine that was previously provided by tobacco products with nicotine provided through a lozenge, gum, patch, or other delivery method. These alternate nicotine delivery formats are safer than tobacco products and aid tobacco users who are trying to quit by relieving nicotine cravings and controlling many of the symptoms associated with quitting tobacco. As a result, the use of NRT improves quit outcomes versus quit attempts using will power alone.

Research has shown that, in combination with NRT, behavioral support is important to help a smoker successfully quit. Various triggers, such as social activities, revisiting locations, stress or even boredom can cause a quitting smoker to have a craving, which can lead to a relapse and a resumption of their tobacco habit. Nicotine cessation behavioral support, which can be reinforced and optimized using mobile device technology, can help tobacco users identify and predict these triggers so they can be more prepared to defeat them. In addition, nicotine cessation behavioral support can track success milestones, the use of NRT products, or if they slip up and use a tobacco product during the quitting process. All of this information helps quitters understand their habits and needs, so they can increase the odds that they will successfully quit tobacco.

A downside to existing nicotine cessation behavioral support plans that use a mobile device is the length of time and the specific actions required to log an event (craving, NRT use or tobacco event). The fast pace of daily life, social norms regarding situational mobile phone usage and the spontaneous nature of cravings can make the act of accessing a mobile device and manually entering information prohibitively time consuming or socially awkward. As a result, using currently available nicotine cessation behavioral support apps on mobile devices in real-time can invite undesired scrutiny from third parties. To avoid this scrutiny, the quitter may not enter data or may opt to batch enter retrospective data when it is convenient, but this is likely to reduce both the quantity and accuracy of the information—which will lead to inferior nicotine cessation behavioral support. What is needed is a discreet device that can be used in conjunction with an application on a mobile device to collect real-time information that will be used to create a personalized nicotine cessation behavioral support plan.

SUMMARY

Embodiments can provide a wearable device for enhanced nicotine cessation behavioral support, comprising a body comprising a top surface, a first surface, a second surface, and an underside surface; a processor located within the body; a communication device located within the body in communication with the processor; one or more buttons in communication with the processor; an internal storage medium located within the body in communication with the processor; and a power supply located within the body; wherein the one or more buttons are configured to trigger the processor to log a NRT use event to the internal storage medium when depressed and subsequently released within a predetermined timeframe; wherein the one or more buttons are configured to trigger the processor to log a tobacco use event to the internal storage medium when depressed and released at a time longer than the predetermined timeframe; wherein the one or more buttons, when depressed, are configured to trigger the processor to log a craving event to the internal storage medium, wherein an intensity of the craving event is determined by a time duration between depression and release of the one or more buttons.

Embodiments can further provide a wearable device further comprising one or more illumination devices configured to illuminate during at least one of: an event logging or a data synch.

Embodiments can further provide a wearable device wherein the logging of the NRT use event is illustrated by illuminating at least one of the one or more illumination devices.

Embodiments can further provide a wearable device wherein the logging of the tobacco usage event is illustrated by illuminating at least two of the one or more illumination devices.

Embodiments can further provide a wearable device wherein the intensity of the craving event is illustrated by illuminating at least one of the one or more illumination devices.

Embodiments can further provide a wearable device configured to transfer one or more stored events in the internal storage medium to a mobile device running a nicotine cessation behavioral support application through the communication device when any of the one or more buttons are depressed and released.

Embodiments can further provide a wearable device further comprising a GPS module located within the body in communication with the processor; wherein the wearable device records a location of the wearable device at the time any of the NRT use, tobacco use, or craving events are logged.

Embodiments can further provide a wearable device further comprising a heart rate monitor located within the body in communication with the processor; wherein the wearable device records a heart rate of the user at the time any of the NRT use, tobacco use, or craving events are logged.

Embodiments can further provide a wearable device further comprising an accelerometer located within the body in communication with the processor; wherein the wearable device records the orientation of the wearable device at the time any of the NRT use, tobacco use, or craving events are logged.

Embodiments can further provide a wearable device wherein the power supply is a rechargeable battery.

Embodiments can further provide a wearable device wherein the power supply is a non-rechargeable battery.

Embodiments can further provide a wearable device wherein the power supply is provided on the underside surface of the wearable device at an angle in relation to a X axis of the wearable device or a X axis of a circuit board assembly to which the power supply is mounted.

Embodiments can further provide a wearable device wherein the angle of the power supply is in the range of 10 degrees to 20 degrees in relation to the X axis of the wearable device or the X axis of the circuit board assembly to which the power supply is mounted.

Embodiments can further provide a wearable device wherein the one or more buttons comprise a first button located on the top surface of the wearable device.

Embodiments can further provide a wearable device wherein the one or more buttons further comprise a second button located on the first surface of the wearable device, and a third button located on the second surface of the wearable device.

Embodiments can further provide a wearable device wherein the first button is configured to trigger the processor to log the NRT use and tobacco use events.

Embodiments can further provide a wearable device wherein the second button and the third button are configured to trigger the processor to log the craving events.

Embodiments can further provide a method for reinforcing nicotine cessation behavioral support using a wearable device, comprising generating, by a wearable device, one or more logged events comprising at least one of a NRT use event, a tobacco use event, or a craving event; detecting, by the wearable device, if a mobile device is present; if the mobile device is present, sending, by the wearable device, each of the one or more logged events to the mobile device, wherein the mobile device is running a nicotine cessation behavioral support application; providing, via the nicotine replacement therapy application, feedback to a user in order to encourage the user to cease the use of tobacco products; wherein the NRT use event is generated by the depression and release within a predetermined timeframe of one or more buttons of the wearable device; wherein the tobacco use event is generated by the depression and release after a predetermined timeframe of one or more buttons of the wearable device; wherein the craving event is generated by depression and release of one or more buttons of the wearable device in conjunction, wherein the intensity of the craving event is determined by a time duration between depression and release of the one or more buttons.

Embodiments can further provide a method further comprising if the mobile device is not present, storing each of the logged events in an internal storage of the wearable device.

Embodiments can further provide a method further comprising determining, by the wearable device, a renewed presence of the mobile device; pushing all stored logged events to the mobile device; and deleting all stored logged events from the internal storage medium.

Embodiments can further provide a method further comprising illuminating one or more illumination devices during the generation of any of the one or more logged events.

Embodiments can further provide a method wherein providing feedback further comprises motivational messages or quit benefits.

Embodiments can further provide a method wherein providing feedback further comprises displaying an NRT progress timeline or time since last tobacco use.

Embodiments can further provide a method wherein providing feedback further comprises displaying one or more coupons for NRT products.

Embodiments can further provide a method wherein providing feedback comprises displaying a graphical representation of a corpus of prior logged events.

Embodiments can further provide a method wherein the feedback comprises one or more coupons for NRT products.

Embodiments can further provide a system for nicotine cessation behavioral support, comprising a wearable device comprising a body comprising a top surface, a first surface, a second surface, and an underside surface, a processor located within the body; a communication device located within the body in communication with the processor; a first button in communication with the processor, located on the top surface; a second button in communication with the processor, located on the first surface; a third button in communication with the processor, located on the second surface; one or more illumination devices in communication with the processor; an internal storage medium located within the body in communication with the processor; and a power supply located within the body; wherein the first button is configured to trigger the processor to log a NRT use event to the internal storage medium when depressed and subsequently released within a predetermined timeframe; wherein the first button is configured to trigger the processor to log a tobacco use event to the internal storage medium when depressed and released at a time longer than the predetermined timeframe; wherein the second or third buttons, when depressed, are configured to trigger the processor to log a craving event to the internal storage medium, wherein an intensity of the craving event is determined by a time duration between depression and release of the second or third buttons; wherein at least one of the one or more illumination devices are configured to illuminate during the logging of the NRT use event, the tobacco use event, or the craving event; and a mobile device configured to run an NRT application; wherein the wearable device is configured to transfer one or more stored events in the internal storage medium to the mobile device through the communication device when any of the one or more buttons are depressed and released; wherein the NRT application is configured to provide a user with one or more feedback actions in response to the stored events received from the wearable device.

BRIEF DESCRIPTION OF THE DRAWING FIGURES

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

Figure 10:
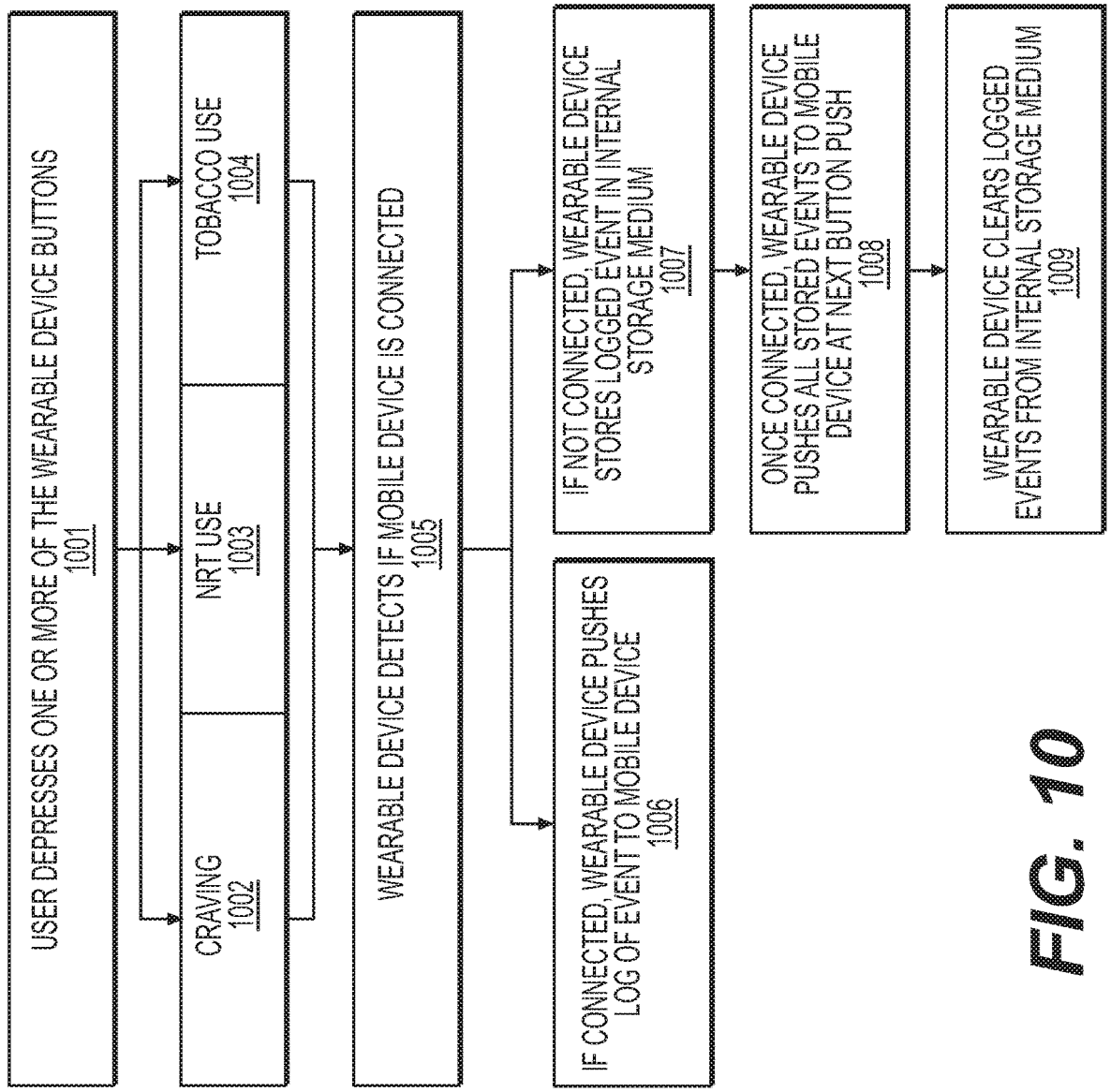
Figure 11:
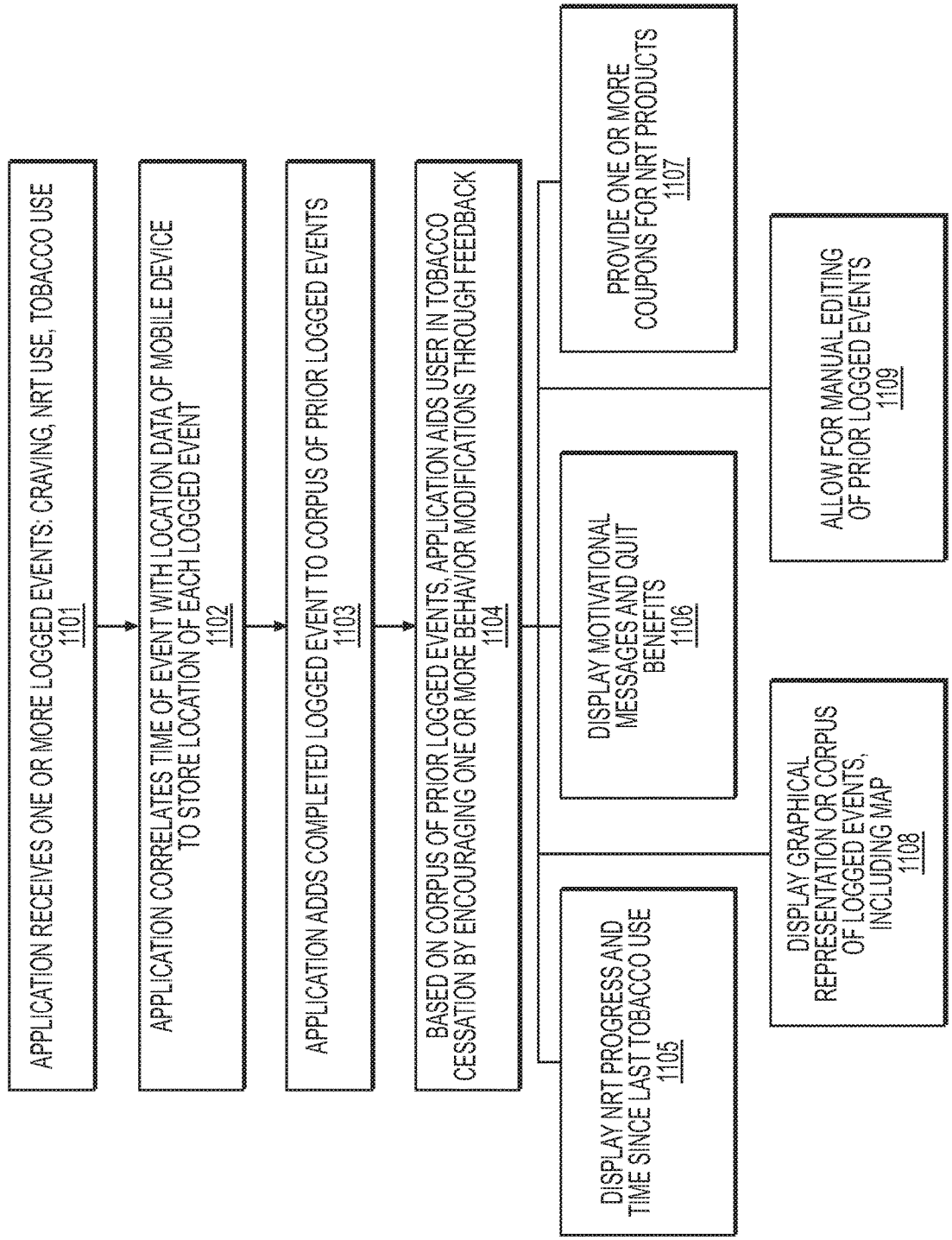
Figure 12:
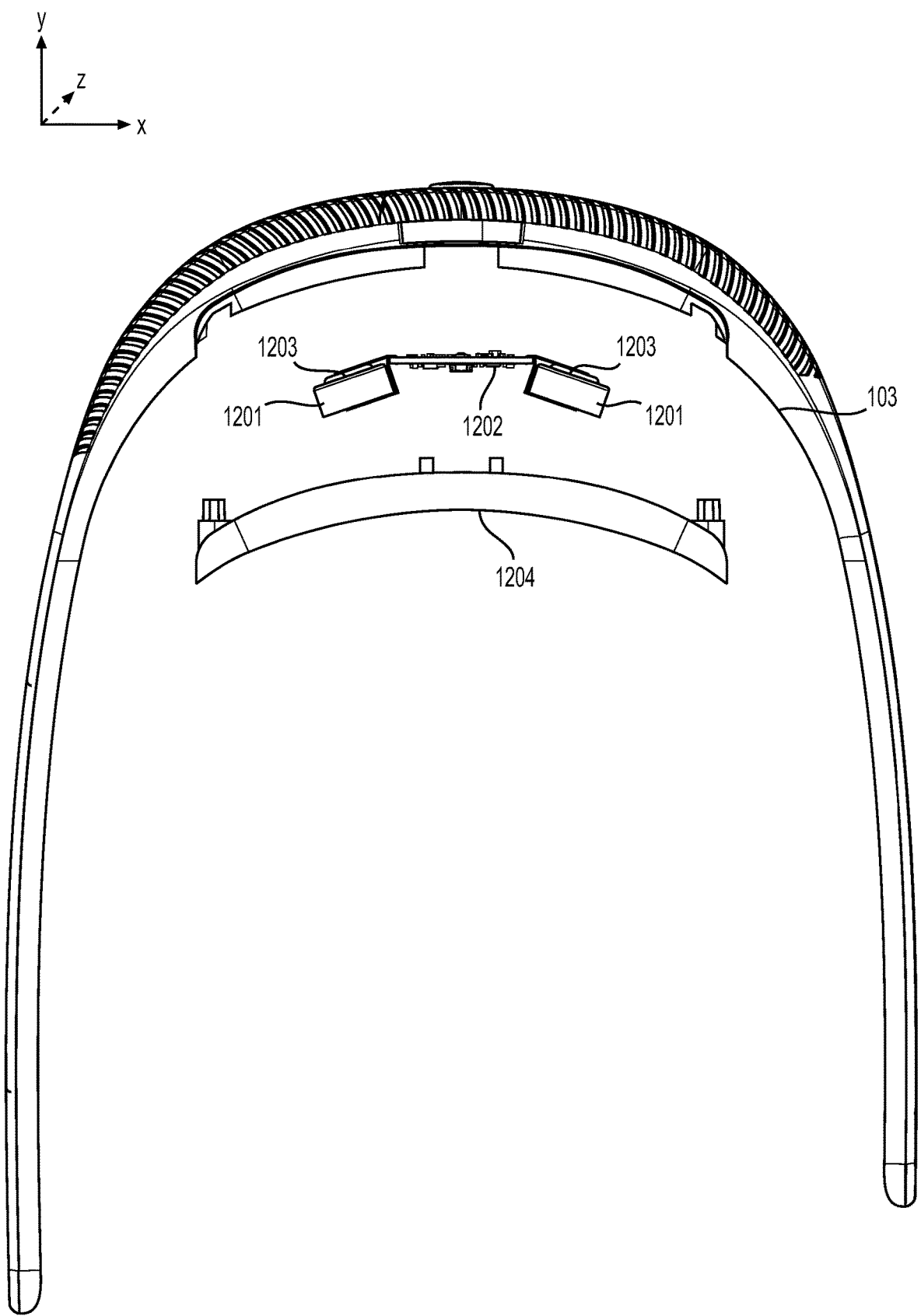

FIG. 10 illustrates a flowchart depicting the functionality of a wearable device for nicotine cessation behavioral support, in accordance with embodiments described herein; and FIG. 11 illustrates a flowchart depicting the functionality of a nicotine cessation behavioral support application to be run on a mobile device and configured to interact with a wearable device for nicotine replacement therapy;

FIG. 12 illustrates an exploded view of a wearable device for nicotine cessation behavioral support depicting components of the underside surface, in accordance with embodiments described herein.

DETAILED DESCRIPTION

Embodiments of the present invention involve a wearable device that can be paired with a mobile device running an application for use in nicotine cessation behavioral support, which can be paired with the use of nicotine replacement therapies (NRT). During the process of quitting the use of tobacco products, one or more events can occur either individually, in sequence, or in any combination: the use of a NRT product, the use of a tobacco product (also called a slip-up), or the user can have a craving for a tobacco product. Previously, the user could log any of these three events using an application on a mobile device. The present invention introduces a wearable device that can discreetly log and store these events, along with other information, for eventual synching and processing by the application.

The addition of a physical wearable device can provide a tangible reminder to the user about their desire to quit tobacco products, and provide physical reinforcement if behavioral modification alone proves too difficult. Additionally, the wearable device can help provide the user with a trackable record of all potential triggers to re-using tobacco products, allowing the user a more informed roadmap to behavioral modification that can prove more effective than without the wearable device. The wearable device can be considered an "active" device, in that it requires user input in addition to its functions. This is in contrast to other "passive" devices, which merely monitor and report without the ability to accept user input.

Figure 1:
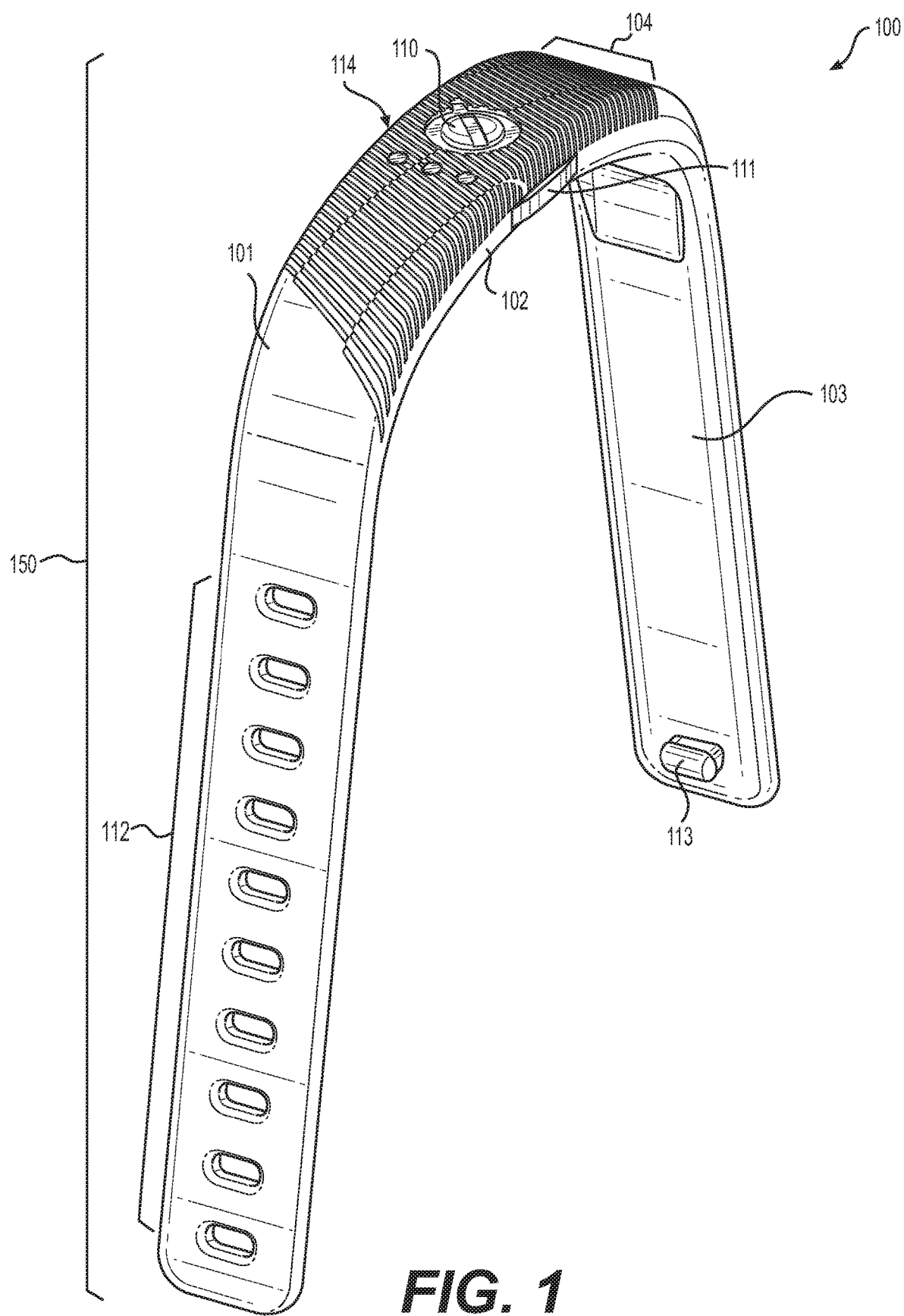
FIG. 1 illustrates a perspective view of a wearable device for nicotine cessation behavioral support, in accordance with embodiments described herein.
Figure 3:
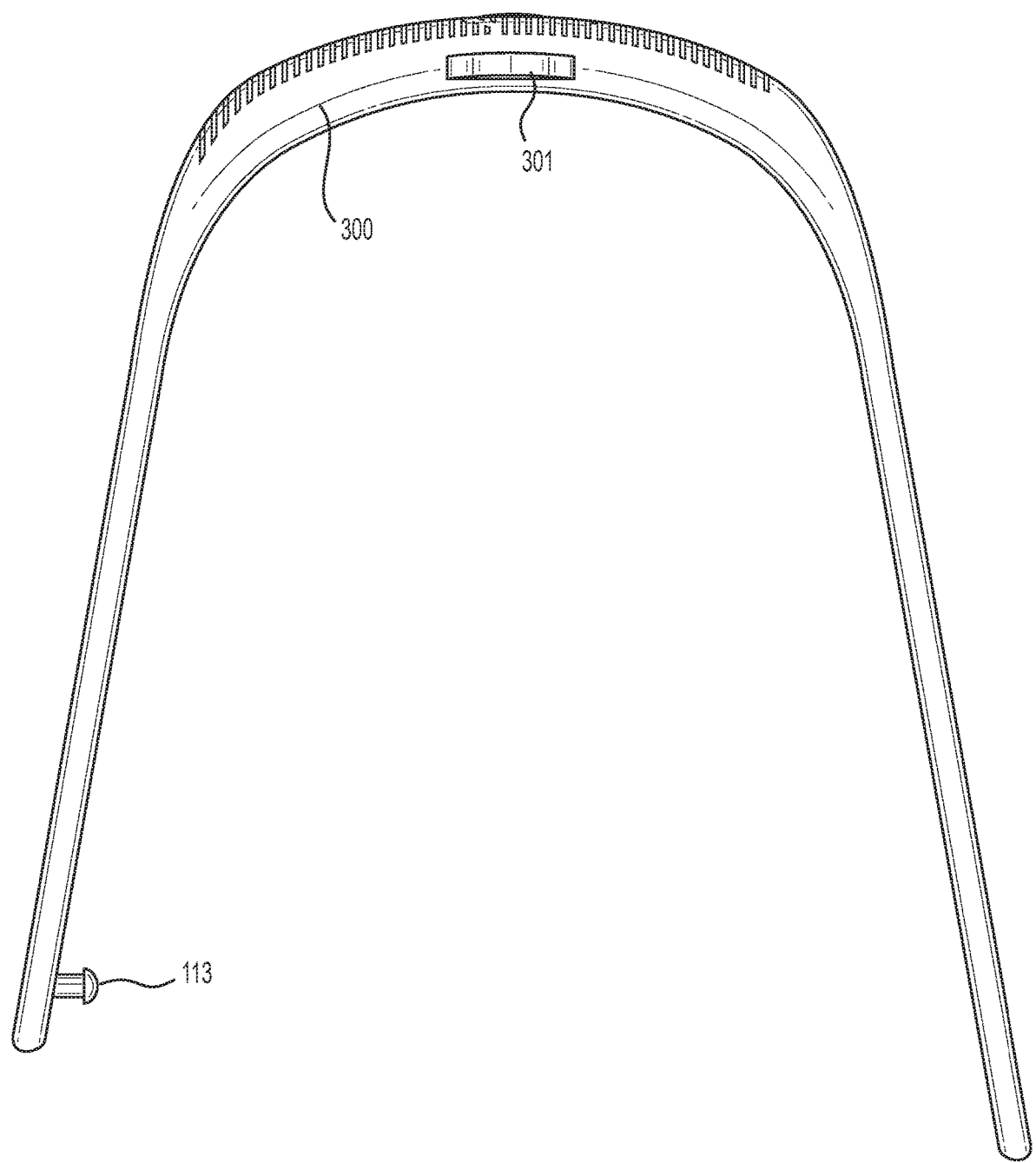
FIG. 3 illustrates a side view of a wearable device for nicotine cessation behavioral support depicting a second surface, in accordance with embodiments described herein.

FIG. 1 illustrates a perspective view of a wearable device for nicotine cessation behavioral support, in accordance with embodiments described herein. The wearable device 100 can have a body 150 comprising a top surface 101, a first surface 102, a second surface 300 (as shown in FIG. 3), and an underside surface 103. The wearable device 100 can have one or more buttons, which can include a first button 110, which in an embodiment can be located on the top surface 101 of the wearable device 100, a second button 111, which in an embodiment can be located on the first surface 102 of the device, and a third button 301 (as shown in FIG. 3), which in an embodiment can be located on the second surface 300 (as shown in FIG. 3).

The first button 110, second button 111, and third button 301 can be used to log one or more events within an internal storage medium housed within the body of the wearable device 100. In an embodiment, the first button 110 can be used to log a first event if quickly depressed and released and a second event if depressed, held, and then released. In an embodiment, the first event can correspond to the user having used NRT, in particular using gum or a lozenge. In an embodiment, the second event can correspond to the user having consumed a tobacco product, also known as a slip-up. The second button 111 and the third button 301, when depressed either singularly or in conjunction, can be used to log a third event. In an embodiment, the third event can correspond to the user experiencing a craving for a tobacco product.

The wearable device 100 can have a set of one or more illumination devices 114, which can be used to illustrate the logging or intensity of any first, second, and/or third events recorded by the user using the first button 110, second button 111, or third button 301. During a logging of any of the three types of events, the one or more illumination devices 114 can light up in their individual capacity, or in any combination. In an embodiment, each of the one or more illumination devices can have a different color.

For instance, if a user logs a craving event, the intensity of the craving can be displayed by the one or more illumination devices by the illumination devices illuminating in a sequential manner, i.e. one illumination device (mild craving), then two (medium craving), then three (intense craving), as the user continues to hold the button(s) on the wearable device for a longer duration. When the button(s) are released, the illumination devices can extinguish, and the craving event, along with its intensity, can be logged into the internal storage medium of the wearable device.

The one or more illumination devices 114 (also shown as 601-603 in FIG. 6) can be LED or other low-power light sources embedded within the internal circuitry of the wearable device 100, and can be recessed within the wearable device 100 but have their light transmitted to the surface of the top surface 101 of the wearable device 100 through one or more light channels that correspond with the one or more illumination devices 114.

The position, number, location, and function of the buttons and the one or more illumination devices is illustrative only, and any combination of number, location, and function is possible.

The top surface 101 of the wearable device 100 can have an area of texturing 104. To secure the wearable device 100 to a user, one or more adjustment holes 112 can be cut into the wearable device, into which a clasp 113 can be inserted to secure the wearable device 100 to the user. In an embodiment, the wearable device 100 can be worn on the user's wrist, as illustrated in the Figures. In an embodiment, the exterior of the wearable device can be made of a waterproof material, such as rubber, silicone, plastic, treated animal materials, metal, or any combination thereof.

Figure 2:
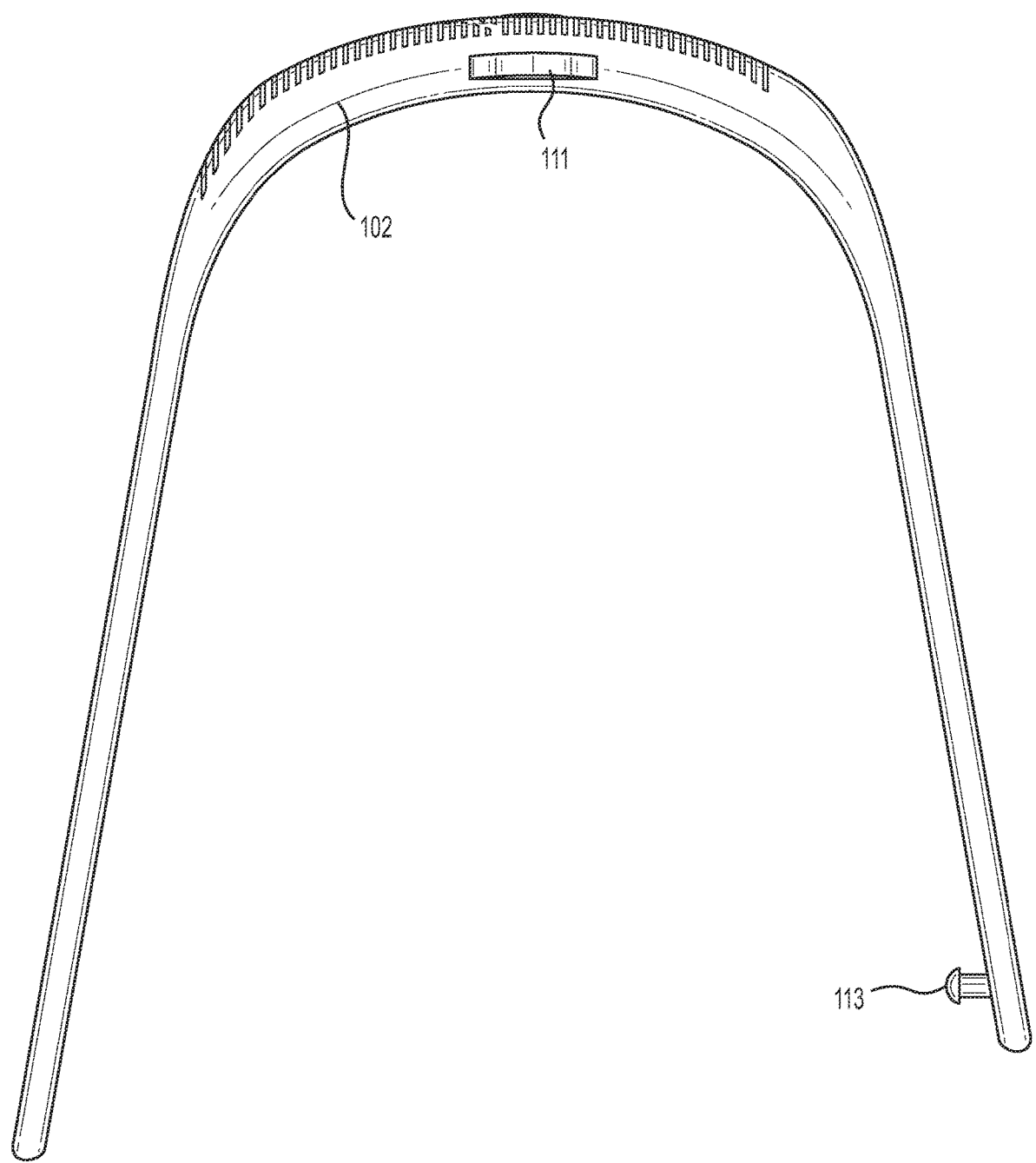
FIG. 2 illustrates a side view of a wearable device for nicotine cessation behavioral support depicting a first surface, in accordance with embodiments described herein.

FIG. 2 illustrates a side view of a wearable device for nicotine cessation behavioral support depicting a first surface, in accordance with embodiments described herein. The second button 111 can be mounted on the first surface 102 such that depressing and releasing the second button 111 can be done in a squeezing motion. From this view, the clasp 113 is visible, which can be used to secure the wearable device to the user.

FIG. 3 illustrates a side view of a wearable device for nicotine cessation behavioral support depicting a second surface, in accordance with embodiments described herein. The third button 301 can be mounted on the second surface 300 such that depressing and releasing the third button 301 can be done in a squeezing motion, which can be an unobtrusive motion easily performed without notice by other persons, which may be desirable by the user so as not to draw attention to the fact that the user is attempting to quit tobacco products. From this view, the clasp 113 is visible, which can be used to secure the wearable device to the user.

Figure 4:
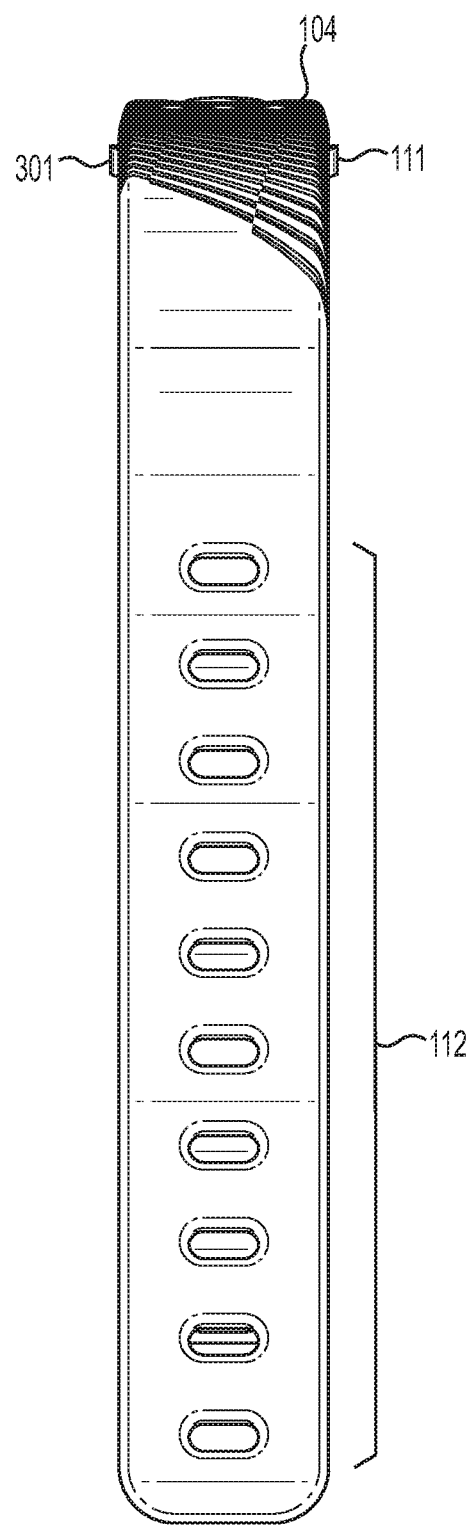
FIG. 4 illustrates a side view depicting the top surface of a wearable device for nicotine cessation behavioral support, in accordance with embodiments described herein.
Figure 5:
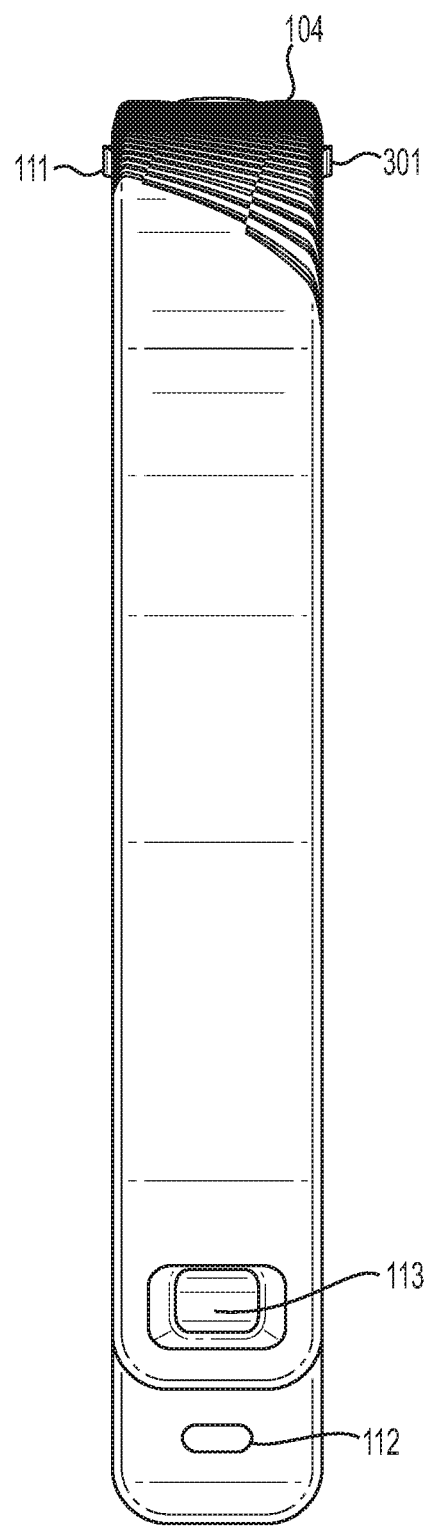
FIG. 5 illustrates an alternate side view depicting a top surface of a wearable device for nicotine cessation behavioral support, in accordance with embodiments described herein.

FIGS. 4 and 5 illustrate side views depicting the top surface of a wearable device for nicotine cessation behavioral support, in accordance with embodiments described herein. As shown the one or more adjustment holes 112 can be used in conjunction with the clasp 113 to secure the wearable device to the user. The second button 111 and the third button 301 can be placed on opposite sides of the wearable device, such that depressing the second button 111 and the third button 301 simultaneously can be accomplished by a squeezing motion. Also shown is the area of texturing 104 that can be located on the top surface of the wearable device.

Figure 6:
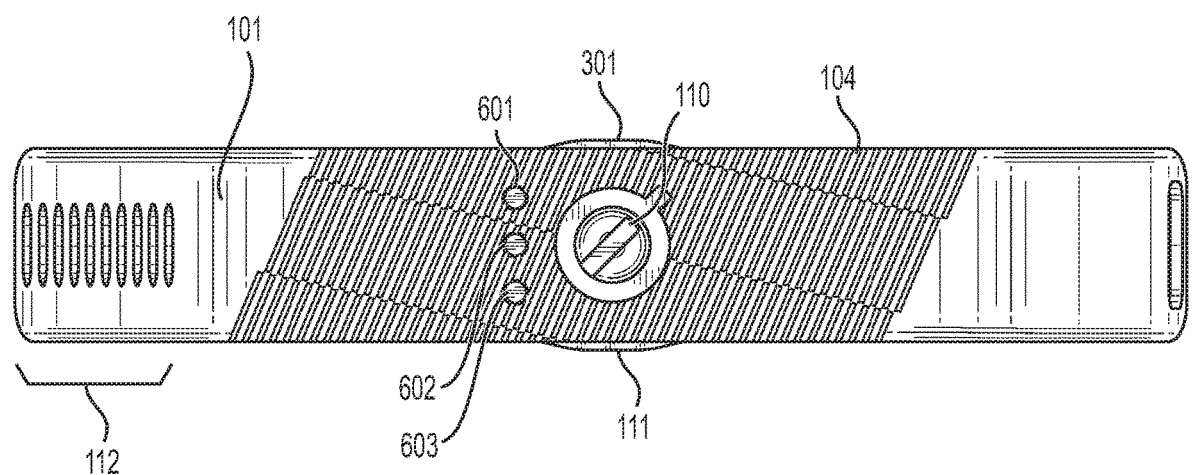
FIG. 6 illustrates a top view of a wearable device for nicotine cessation behavioral support, in accordance with embodiments described herein.

FIG. 6 illustrates a top view of a wearable device for nicotine cessation behavioral support, in accordance with embodiments described herein. As shown in this view, the first button 110 can be stylized such that the first button 110 is easily felt by a user's fingers. The one or more illumination devices can include a first illumination device 601, a second illumination device 602, and a third illumination device 603, each of which can illuminate individually, or in any combination, to denote an action of the wearable device, including but not limited to a logged event, the pushing of a logged event to a connected mobile device, or a power supply charge level. In an embodiment, each of the first illumination device 601, second illumination device 602, and third illumination device 603 can be light producing elements directly attached to the internal circuitry of the wearable device, and the light from those elements can be translated to the surface of the wearable device through corresponding light channels. Alternately, the illumination devices can be light producing elements adhered directly to the surface of the top surface of the wearable device.

In an embodiment, the second button 111 and the third button 301 can be located on the sides of the wearable device substantially in the same position of the first button 110, such that the user can easily find any of the three buttons to log a particular event.

Figure 7:
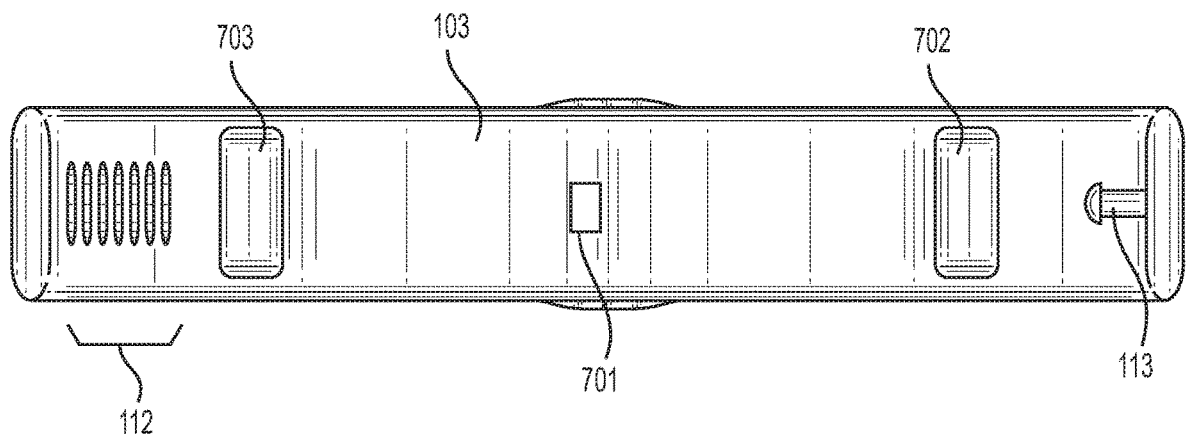
FIG. 7 illustrates an underside surface view of a wearable device for nicotine cessation behavioral support, in accordance with embodiments described herein.

FIG. 7 illustrates an underside surface view of a wearable device for nicotine cessation behavioral support, in accordance with embodiments described herein. In an embodiment, the underside surface 103 can be made of a different material than the top surface of the wearable device and its associated bands. Alternately, the entire outer surface of the wearable device can be formed from the same material. In an embodiment, the underside surface 103 can be snap fit onto the wearable device 100 or can be screwed onto the device. In either instance, the underside surface 103 can be sealed on the wearable device 100 such that the fit is water tight. In an embodiment, the underside surface 103 of the wearable device can have an opening for a heart rate monitor 701, which can be placed at a central location on the underside surface 103 of the wearable device such that the heart rate monitor 701 can be securely positioned on the user's wrist at an optimal location to derive heart rate data. In an embodiment, the underside surface 103 of the wearable device can have a first flexpoint 702 and a second flexpoint 703, which can be used to allow the wearable device to bend such that it encircles a user's wrist, and can be secured through the clasp 113 being secured in one of the adjustment holes 112.

Figure 8:
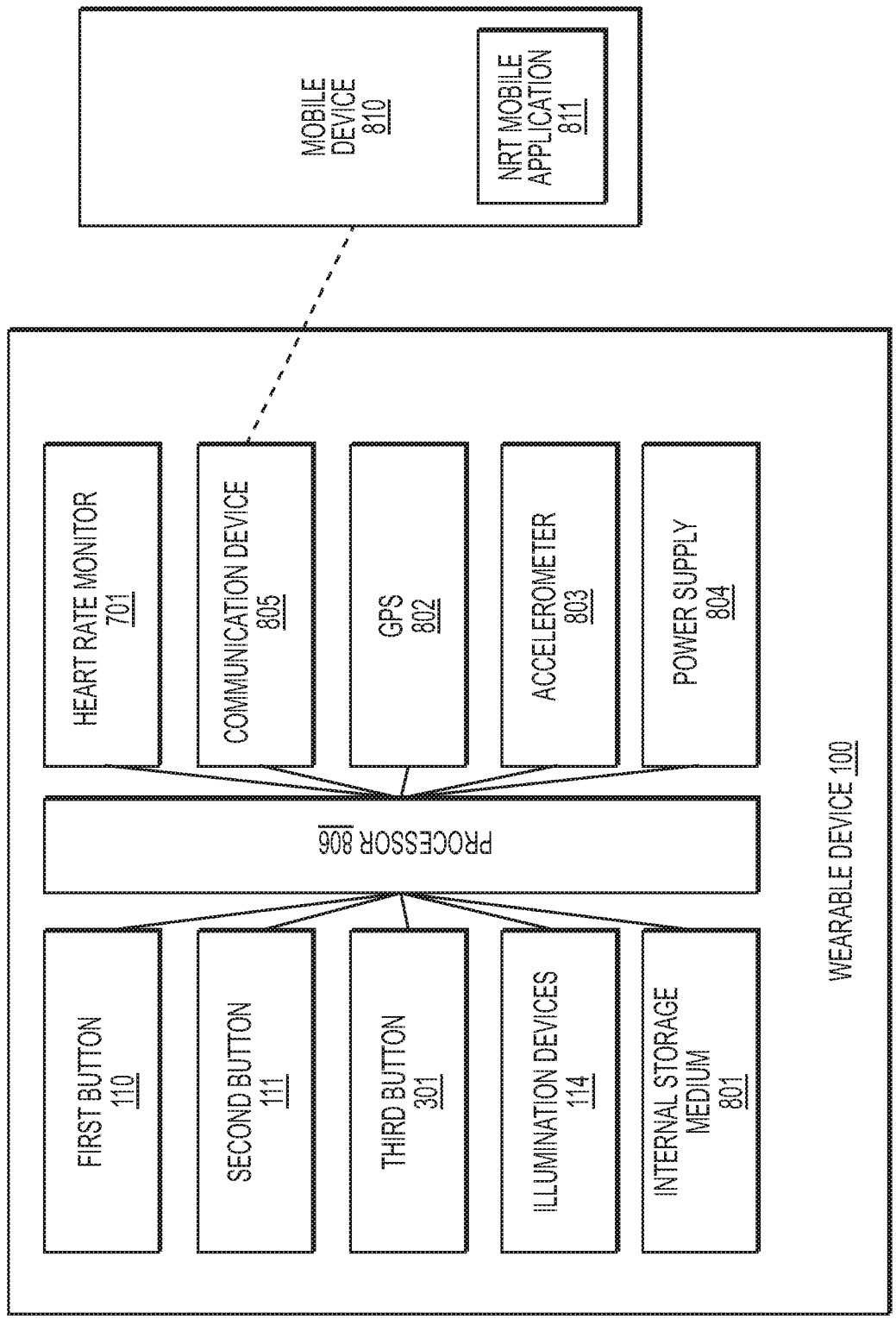
FIG. 8 illustrates a block diagram depicting the components of a wearable device for nicotine cessation behavioral support, in accordance with embodiments described herein.

FIG. 8 illustrates a block diagram depicting the components of a wearable device for nicotine cessation behavioral support, in accordance with embodiments described herein. As described previously, the wearable device 100 can have a first button 110, second button 111, and third button 301, which, when pressed individually or in a particular combination, can trigger the logging of a number of events. The logged events can be stored in an internal storage medium, which can be conventional digital storage sufficient to store a large number of logged events. The wearable device 100 can have one or more illumination devices 114 that can be used to display information about the actions of the wearable device, as described above. In addition, the wearable device 100 can have a communication device 805, which can use a wireless signal, such as Bluetooth or WiFi, to connect to a mobile device 810 such that an event logged by the wearable device 100 can be transferred to the mobile device 810, which can run an application for nicotine cessation behavioral support 811, when the mobile device 810 is connected. Additionally, the wearable device can have a power supply 804, which can be disposable or rechargeable batteries. In an embodiment, the batteries can be non-removable and secured in the device for the duration of the life of the device, which may require a user to replace the wearable device 100 when the power supply 804 is fully drained.

FIG. 12 illustrates an exploded view of the components of the underside surface of the wearable device for nicotine cessation behavioral support, in accordance with embodiments described herein. As shown in FIG. 12, the disposable or rechargeable batteries 1201 can be arranged at an angle in relation to the X axis of the wearable device 100 or the X axis of a printed circuit board assembly 1202 to which the disposable or rechargeable batteries 1201 can be mounted. The angle of the disposable or rechargeable batteries 1201 can correspond to the curve or slope of the underside surface 103 of the wearable device 100. This arrangement of the disposable or rechargeable batteries 1201 allows for the wearable device 100 to fit securely and discreetly along the curvature of the user's wrist. Thus, the wearable device 100 can be worn subtly and can be easily manipulated by the user to log an event. The angle of the disposable or rechargeable batteries 1201 can be in the range of 10 degrees to 20 degrees in relation to the X axis of the wearable device 100 or the X axis of the printed circuit board 1202. Preferably, the angle of the disposable or rechargeable batteries 1201 in relation to the X axis of the wearable device 100 or the X axis of the printed circuit board 1202 is 15 degrees. A cover of the underside surface 1204 can be sealed, attached, secured, or otherwise fixed onto the wearable device 100 to prevent unwanted detachment during normal use of the wearable device 100. The cover of the underside surface 1204 can also be sealed onto the wearable device 100 such that the fit is water tight. The position, number, and location of the disposable or rechargeable batteries 1201 is illustrative only, and any combination of position, number, and location is possible.

Furthermore, the disposable or rechargeable batteries 1201 can be held in place by tabs 1203. The tabs 1203 prevent the disposable or rechargeable batteries 1201 from moving while also ensuring the safety of the user and the reliability of the wearable device 100.

Additional components of the wearable device 100 can include: a heart rate monitor 701, which can be used to track the user's heart rate at the time an event is logged; a GPS module 802, which can be used to record a user's location at the time an event is logged; and an accelerometer 803, which can be used to track the motion of the wearable device 100 at the time an event is logged. All of the components of the wearable device 100 can be configured to communicate with a processor 806, which can be a single-core or multi-core processor.

Figure 9:
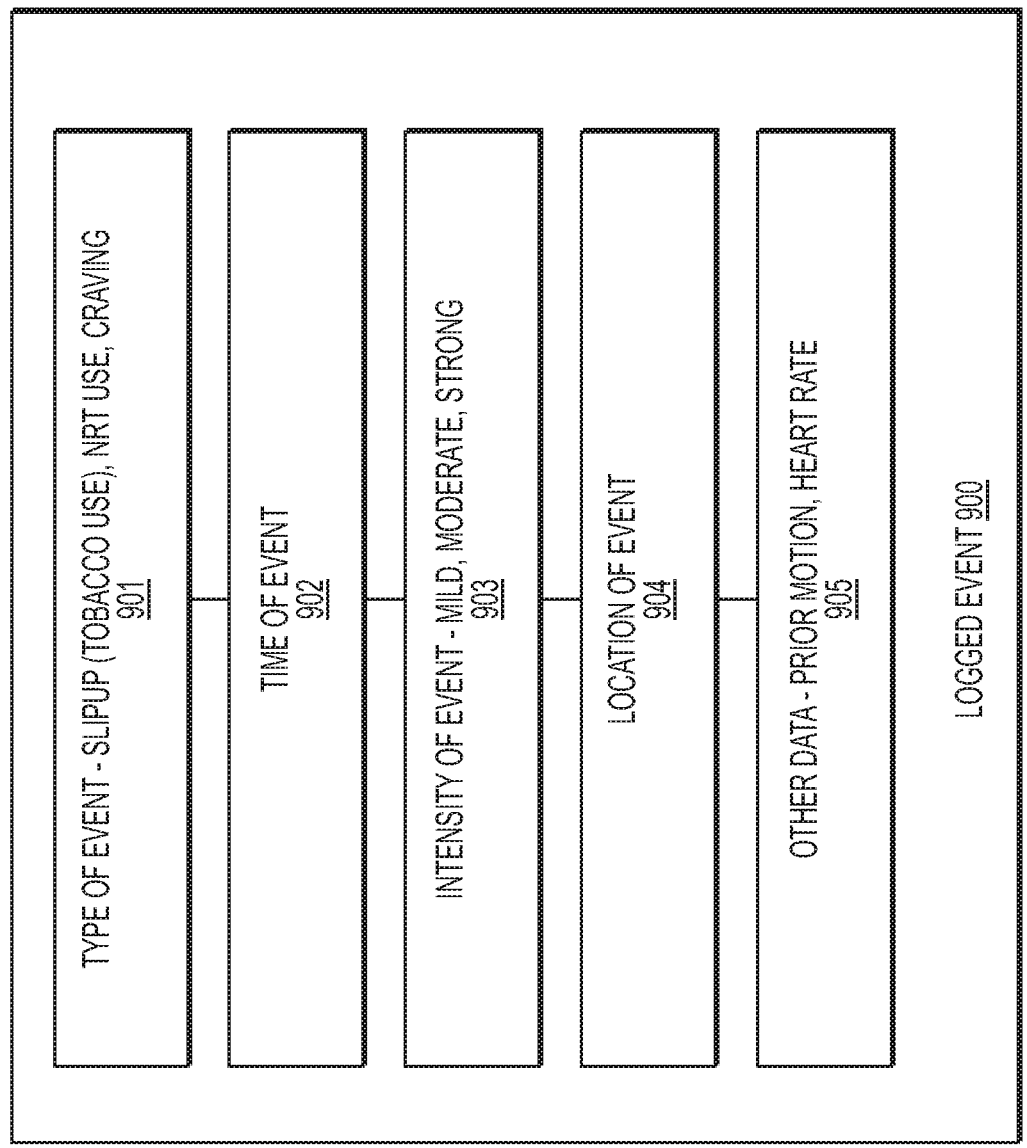
FIG. 9 illustrates a block diagram depicting the components of an event logged by a wearable device for nicotine cessation behavioral support, in accordance with embodiments described herein.

FIG. 9 illustrates a block diagram depicting the components of an event logged by a wearable device for nicotine cessation behavioral support, in accordance with embodiments described herein. The primary component of a logged event 900 is the type of event 901, which can be determined based on the button combination used to trigger the event logging. In an embodiment, a logged event 900 can be one of three types: a slipup (i.e., the user has used a tobacco product), NRT use (i.e., the user has used some form of NRT, such as nicotine-infused gum or lozenges), or a craving (i.e., the user desired to use a tobacco product, but did not do so). In addition to the type of the event 901, the logged event can include a time of the event 902, which can be used by the wearable device or the mobile device to order and sort logged events in the event of a bulk download (such as when the wearable device has been out of contact with the mobile device for multiple event loggings).

For a craving event, the wearable device can also record the intensity of the event 903, which in an embodiment can be mild, moderate, or strong. The intensity of the event 903 can be set by the user by the duration one of the buttons is pushed and then subsequently released. For example, the user can depress either or both of the second and third buttons, hold the button(s) for a predetermined period of time, and then release. In an embodiment, the illumination devices can illuminate in sequence as the intensity level increases from mild to moderate to strong in order to inform the user as to when to release the triggering button(s). Upon release, the event (including its similarity) is logged.

In an embodiment where the wearable device and/or the mobile device has location-tracking capability, the logged event 900 data can also include the location of the event 904, which can be recorded as latitude and longitude, or through relational data to one or more landmarks. This can be particularly useful for tracking craving and slipup events, and correlating those events and their intensity to particular locational triggers, such as being at a location that serves alcohol or other known behavioral triggers that impede the cessation of tobacco products. With this information, the mobile can application can create a more personalized nicotine cessation behavioral support plan.

Additionally, if the wearable device has components such as a heart rate monitor or an accelerometer, the wearable device can record other data 905 related to the logged event 900, such as the heart rate of the user at the time the event is triggered or any particular orientation or motion sequence of the wearable device at the time of triggering. All components of the logged event 900 can be transferred to the mobile device during synching. With this information, the mobile can application can create a more personalized nicotine cessation behavioral support plan.

FIG. 10 illustrates a flowchart depicting the functionality of a wearable device for nicotine cessation behavioral support, in accordance with embodiments described herein. To initiate an event triggering, the user can depress one or more of the wearable device buttons 1001. Based on the combination of buttons pressed, the type of event can be determined to be a craving event 1002, an NRT use event 1003, or a tobacco use (slipup) event 1004. In an embodiment, the NRT use event 1003 can be triggered by a depression and release of the first button within a predetermined timeframe, the tobacco use event 1004 can be triggered by a depression and release of the first button longer than a predetermined timeframe, and the craving event 1002 can be triggered by the depression and release of the second and third button (either separately or in conjunction), where the intensity of the craving event 1002 can be determined by the length of time between the depression and release of the triggering button(s). Alternately, the intensity of the craving event 1002 can be determined by the number of times the triggering button(s) are depressed and released (i.e. once for mild, twice for moderate, three times for strong).

After the event has been triggered, the wearable device can detect if the mobile device is connected 1005, which can be accomplished through the use of the on-board communication device. In an embodiment, the wearable device can be paired to a single mobile device. In the event the paired mobile device is detected, the wearable device can immediately push the log of the event, with all of its associated data, directly to the mobile device 1006.

In the event the wearable device does not detect that the mobile device is present, the wearable device can store the logged event and its associated data in the internal storage medium 1007. This process can repeat for each event where the mobile device is not connected to the wearable device. At the next instance where the wearable device detects the mobile device upon the logging of an event, the wearable device can push all stored logged events to the mobile device 1008. In an embodiment, the wearable device can determine if the mobile device is connected when any of the wearable device buttons are depressed, independently of whether a particular event is logged (for instance, if the second or third button are depressed individually, as opposed to in conjunction). After pushing all stored logged events to the mobile device 1008, the wearable device can clear all logged events from the internal storage medium 1009, in order to free up storage for the next set of incoming events.

FIG. 11 illustrates a flowchart depicting the functionality of a behavioral support application to be run on a mobile device and configured to interact with a wearable device for nicotine cessation behavioral support. First, the application receives one or more logged events, either through the wearable device, through direct user input to the application, or a combination thereof 1101. The application can then correlate the time of each received event with the location logs of the mobile device in order to store the location of each logged event 1102, in the event the logged events do not already have location data associated. The application can then add the completed logged events to a corpus of prior logged events for the user 1103. Based upon the corpus of prior logged events, the application can aid the user in their goal of nicotine cessation by encouraging one or more behavior modifications through the providing of feedback 1104.

Behavior modification feedback can include positive reinforcement through the display of the user's NRT progress, and can include the time since the user's last tobacco use 1105. Progress and time can be displayed numerically, graphically, in achievement form, as a progress bar, or through other methods of display. The application can motivate the user to continue NRT through the display of motivational messages and quit benefits, which can be positive health and financial outcomes that arise from the cessation of tobacco use. The quit benefits and motivational messages can be tied to the NRT progress of the user (i.e., a user two days into NRT can receive different messages than a user six months into NRT). The application can provide one or more coupons for NRT products 1107 to encourage continued compliance with the NRT regime chosen by the user. In order to encourage the user to avoid locations that trigger relapse behaviors, the application can display a graphical representation of the corpus of logged events 1108, which can include an interactive map that can display any or all of the tobacco use, craving, or NRT use events logged by the user. The application can also allow for a manual editing of prior logged events 1109, such as when the user may desire to increase or decrease the intensity of a logged craving event, or fine-tune the location information of a particular logged event.

The wearable device and nicotine cessation behavioral support application described above are preferred embodiments of the invention, however, alternate embodiments are contemplated. In alternate embodiments, the wearable device can be worn on a user's finger in a ring; around the user's waist in a belt; or around the user's chest or neck in a pendant or necklace. Alternate securing methods can be used to secure the wearable device to the user, such as buckles, fasteners, butterfly clasps, flip clasps, security clasps, or band clasps. In alternate embodiments, the wearable device can be used in conjunction with other behavioral support therapies, such as what is required for weight-loss or other additive behaviors.

The present description and claims may make use of the terms "a," "at least one of," and "one or more of," with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples are intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the example provided herein without departing from the spirit and scope of the present invention.

The system and processes of the figures are not exclusive. Other systems, processes, and menus may be derived in accordance with the principles of embodiments described herein to accomplish the same objectives. It is to be understood that the embodiments and variations shown and described herein are for illustration purposes only. Modifications to the current design may be implemented by those skilled in the art, without departing from the scope of the embodiments. As described herein, the various systems, subsystems, agents, managers, and processes can be implemented using hardware components, software components, and/or combinations thereof. No claim element herein is to be construed under the provisions of 35 U.S.C. 112, sixth paragraph, unless the element is expressly recited using the phrase "means for."

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A wearable device for nicotine cessation behavioral support, comprising:
    a body comprising a top surface, a first surface, a second surface, and an underside surface;
    a processor located within the body;
    a communication device located within the body in communication with the processor;
    one or more buttons in communication with the processor;
    an internal storage medium located within the body in communication with the processor; and
    a power supply located within the body;
    wherein the one or more buttons are configured to trigger the processor to log a nicotine replacement therapy (NRT) use event to the internal storage medium when depressed and subsequently released within a predetermined timeframe;
    wherein the one or more buttons are configured to trigger the processor to log a tobacco use event to the internal storage medium when depressed and released at a time longer than the predetermined timeframe;
    wherein the one or more buttons, when depressed, are configured to trigger the processor to log a craving event to the internal storage medium, wherein an intensity of the craving event is determined by a time duration between depression and release of the one or more buttons.

2. The wearable device as recited in claim 1, further comprising:
    one or more illumination devices configured to illuminate during at least one of: an event logging or a data synch.

3. The wearable device as recited in claim 2, wherein the logging of the NRT use event is illustrated by illuminating at least one of the one or more illumination devices.

4. The wearable device as in one of claims 2-3, wherein the logging of the tobacco use event is illustrated by illuminating at least two of the one or more illumination devices.

5. The wearable device as in one of claims 2-4, wherein the intensity of the craving event is illustrated by illuminating at least one of the one or more illumination devices.

6. The wearable device as in one of claims 1-5, wherein the wearable device is configured to transfer one or more stored events in the internal storage medium to a mobile device running a nicotine cessation behavioral support application through the communication device when any of the one or more buttons are depressed and released.

7. The wearable device as in one of claims 1-6, further comprising:
    a GPS module located within the body in communication with the processor;
    wherein the wearable device records a location of the wearable device at the time any of the NRT use, tobacco use, or craving events are logged.

8. The wearable device as in one of claims 1-7, further comprising:
    a heart rate monitor located within the body in communication with the processor;
    wherein the wearable device records a heart rate of the user at the time any of the NRT use, tobacco use, or craving events are logged.

9. The wearable device as in one of claims 1-8, further comprising:
an accelerometer located within the body in communication with the processor;
wherein the wearable device records the orientation of the wearable device at the time any of the NRT use, tobacco use, or craving events are logged.

10. The wearable device as in one of claims 1-9, wherein the power supply is a rechargeable battery.

11. The wearable device as in one of claims 1-10, wherein the power supply is a non-rechargeable battery.

12. The wearable device as in one of claims 1-11, wherein the one or more buttons comprise a first button located on the top surface of the wearable device.

13. The wearable device as recited in claim 12, wherein the one or more buttons further comprise a second button located on the first surface of the wearable device, and a third button located on the second surface of the wearable device.

14. The wearable device as in one of claims 12-13, wherein the first button is configured to trigger the processor to log the NRT use and tobacco use events.

15. The wearable device as recited in claim 13, wherein the second button and the third button are configured to trigger the processor to log the craving events.

16. A method for reinforcing nicotine cessation behavioral support using a wearable device, comprising:
generating, by a wearable device, one or more logged events comprising at least one of a nicotine replacement therapy (NRT) use event, a tobacco use event, or a craving event;
detecting, by the wearable device, if a mobile device is present;
if the mobile device is present, sending, by the wearable device, each of the one or more logged events to the mobile device, wherein the mobile device is running a nicotine cessation behavioral support application;
providing, via the nicotine replacement therapy application, feedback to a user in order to encourage the user to cease the use of tobacco products;
wherein the NRT use event is generated by the depression and release within a predetermined timeframe of one or more buttons of the wearable device;
wherein the tobacco use event is generated by the depression and release after a predetermined timeframe of one or more buttons of the wearable device;
wherein the craving event is generated by depression and release of one or more buttons of the wearable device in conjunction, wherein the intensity of the craving event is determined by a time duration between depression and release of the one or more buttons.

17. The method as recited in claim 16, further comprising:
if the mobile device is not present, storing each of the logged events in an internal storage of the wearable device.

18. The method as in one of claims 16-17, further comprising:
determining, by the wearable device, a renewed presence of the mobile device;
pushing all stored logged events to the mobile device; and
deleting all stored logged events from the internal storage medium.

19. The method as in one of claims 16-18, further comprising:
illuminating one or more illumination devices during the generation of any of the one or more logged events.

20. The method as in one of claims 16-19, wherein providing feedback further comprises motivational messages or quit benefits.

21. The method as in one of claims 16-20, wherein providing feedback further comprises displaying an NRT progress timeline or time since last tobacco use.

22. The method as in one of claims 16-21, wherein providing feedback further comprises displaying one or more coupons for NRT products.

23. The method as in one of claims 16-22, wherein providing feedback comprises displaying a graphical representation of a corpus of prior logged events.

24. The method as in one of claims 16-23, wherein the feedback comprises one or more coupons for NRT products.

25. A system for nicotine cessation behavioral support, comprising:
a wearable device comprising:
a body comprising a top surface, a first surface, a second surface, and an underside surface,
a processor located within the body;
a communication device located within the body in communication with the processor;
a first button in communication with the processor, located on the top surface;
a second button in communication with the processor, located on the first surface;
a third button in communication with the processor, located on the second surface;
one or more illumination devices in communication with the processor;
an internal storage medium located within the body in communication with the processor; and
a power supply located within the body;
wherein the first button is configured to trigger the processor to log a nicotine replacement therapy (NRT) use event to the internal storage medium when depressed and subsequently released within a predetermined timeframe;
wherein the first button is configured to trigger the processor to log a tobacco use event to the internal storage medium when depressed and released at a time longer than the predetermined timeframe;
wherein the second or third buttons, when depressed, are configured to trigger the processor to log a craving event to the internal storage medium, wherein an intensity of the craving event is determined by a time duration between depression and release of the second or third buttons
wherein at least one of the one or more illumination devices are configured to illuminate during the logging of the NRT use event, the tobacco use event, or the craving event; and
a mobile device configured to run a nicotine cessation behavioral support application;
wherein the wearable device is configured to transfer one or more stored events in the internal storage medium to the mobile device through the communication device when any of the one or more buttons are depressed and released;
wherein the nicotine cessation behavioral support application is configured to provide a user with one or more feedback actions in response to the stored events received from the wearable device.

* * * * *